United States Patent
Zhu et al.

(10) Patent No.: US 7,463,712 B2
(45) Date of Patent: Dec. 9, 2008

(54) SCATTER CORRECTION FOR X-RAY IMAGING USING MODULATION OF PRIMARY X-RAY SPATIAL SPECTRUM

(75) Inventors: Lei Zhu, Stanford, CA (US); Rebecca Fahrig, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 7 days.

(21) Appl. No.: 11/557,440

(22) Filed: Nov. 7, 2006

(65) Prior Publication Data

US 2007/0268997 A1    Nov. 22, 2007

Related U.S. Application Data

(60) Provisional application No. 60/802,004, filed on May 18, 2006.

(51) Int. Cl.
*G01N 23/00* (2006.01)
(52) U.S. Cl. .............................. 378/7; 378/2
(58) Field of Classification Search ............ 378/2, 378/4, 7, 98.12, 901
See application file for complete search history.

(56) References Cited

U.S. PATENT DOCUMENTS

| | | | | |
|---|---|---|---|---|
| 3,801,785 A | * | 4/1974 | Barrett | 378/2 |
| 3,882,310 A | * | 5/1975 | Barrett | 378/2 |
| 3,950,613 A | * | 4/1976 | Macovski | 378/2 |
| 3,961,188 A | * | 6/1976 | Barrett | 250/303 |
| 3,992,633 A | * | 11/1976 | Braun et al. | 378/2 |
| 4,413,353 A | * | 11/1983 | Macovski et al. | 378/62 |
| 4,651,002 A | * | 3/1987 | Anno | 250/336.1 |
| 4,727,562 A | * | 2/1988 | Belanger | 378/98.4 |
| 4,918,713 A | * | 4/1990 | Honda | 378/98.4 |
| 5,327,476 A | * | 7/1994 | Kemner | 378/98.4 |
| 5,602,895 A | * | 2/1997 | Fivez et al. | 378/98.4 |
| 5,812,629 A | * | 9/1998 | Clauser | 378/62 |
| 7,046,757 B1 | * | 5/2006 | Bani-Hashemi et al. | 378/7 |
| 2002/0031202 A1 | * | 3/2002 | Callerame et al. | 378/57 |
| 2003/0128801 A1 | * | 7/2003 | Eisenberg et al. | 378/19 |
| 2005/0058352 A1 | * | 3/2005 | Deliwala | 382/232 |

OTHER PUBLICATIONS

Maltz et al., Cone Beam X-ray Scatter Removal via Image Frequency Modulation and Filtering, Engineering in Medicine and Biology Society, 2005 IEEE Annual conference, pp. 1854-1857.*
Roder, Amplitude, Phase, and Frequency Modulation, Proceedings of the Institute of Radio Engineers, vol. 19, No. 12, Dec. 1931, pp. 2145-2176.*
Zhu et al., "Scatter correction method for X-ray CT using primary modulation: theory and preliminary results", IEEE Trans Med Imaging. Dec. 25, 2006(12):1573-87.

* cited by examiner

*Primary Examiner*—Courtney Thomas
*Assistant Examiner*—Alexander H Taningco
(74) *Attorney, Agent, or Firm*—Beyer Law Group LLP

(57) ABSTRACT

Scatter radiation in an x-ray imaging system including an x-ray source and an x-ray detector is separated by using amplitude modulation to translate the spatial frequency of a detected x-ray beam to a higher frequency and provide separation from low frequency scatter signal. The low frequency content of the detected x-ray beam is then obtained by demodulating the detected modulated signal.

12 Claims, 15 Drawing Sheets

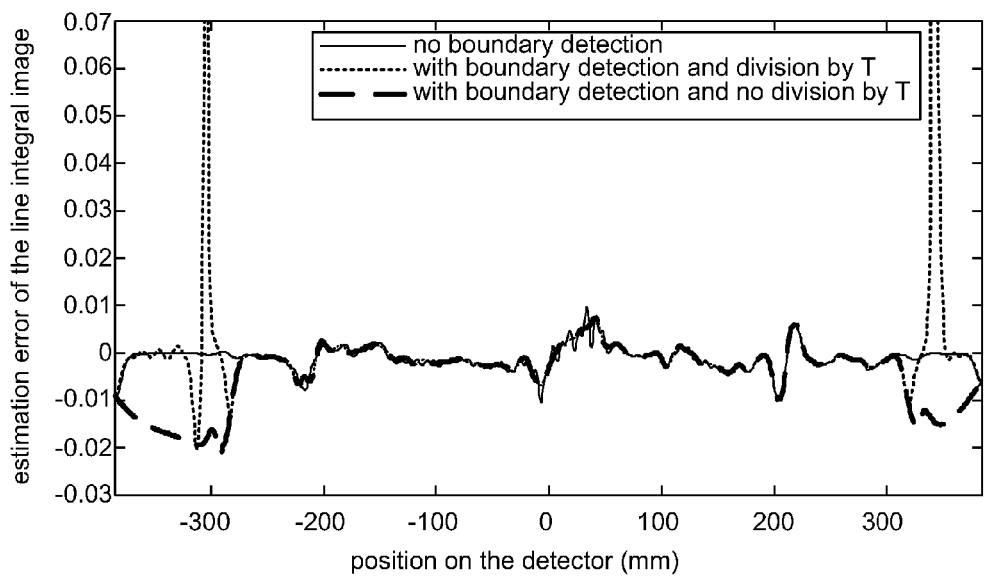
FIG. 11
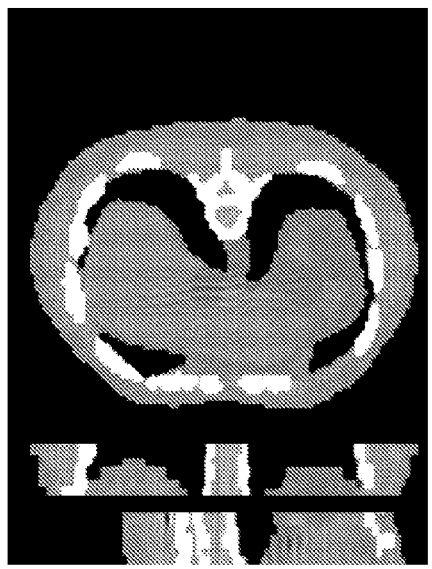 
FIG. 12A          FIG. 12B

$\omega_{max} = \pi/2$ $\omega_{max} = \pi/3$

SCATTER CORRECTION FOR X-RAY IMAGING USING MODULATION OF PRIMARY X-RAY SPATIAL SPECTRUM

CROSS REFERENCE TO RELATED APPLICATIONS

This application claims the benefit of priority under 35 USC 119(e) to U.S. Provisional Application No. 60/802,004, filed May 18, 2006, which is incorporated herein by reference in it's entirety.

STATEMENT REGARDING FEDERALLY SPONSORED RESEARCH OR DEVELOPMENT

The U.S. Government has rights in the disclosed invention pursuant to NIH Grant No. R01 EB003524 to Stanford University.

BACKGROUND OF THE INVENTION

This invention relates generally to x-ray imaging including computed tomography (CT), and more particularly the invention relates to correcting detected CT signals for scatter radiation.

Computer tomography is an established medical technique for visualizing internal organs with high resolution. Both fan beams and cone beams of x-rays are employed in CT An x-ray system with a large area detector, such as is used for cone-beam CT (CBCT), typically has high scatter. Scatter causes severe distortions and contrast loss in the reconstructed images, and developing an effective scatter correction method is still a major challenge. Many methods have been proposed in the literature and provide significant improvement in image quality, although drawbacks still exist. One category of the scatter control techniques includes hardware-based methods, such as anti-scatter grid, air gap, scatter measurement using a beam stop array etc. These approaches suppress or correct for the presence of scatter by modifying the x-ray system. An alternative approach using software-based methods estimates and corrects for the scatter based on the system geometry and imaged object, and it has been shown for some applications that effective scatter control can be achieved. To combine the strengths of different types of correction methods, hybrid approaches are also often used which could provide well balanced tradeoffs among correction effectiveness, calculation time, exposure loss, dose increase, and the like.

The present invention is directed providing an improved method of x-ray scatter estimation in detected CT signals.

SUMMARY OF THE INVENTION

In an x-ray projection, scatter signal concentrates in the low frequency area of k-space, whereas the primary x-ray signal has larger frequency coverage with overlap of the scatter and the low frequency part of the primary signal.

In accordance with the invention, scatter radiation is estimated by first modulating x-rays from an x-ray source, detecting x-ray signals combined from both scatter radiation and from the modulated x-ray beam, low pass filtering the detected x-ray signals to obtain a spectral estimate of the combined scatter x-ray signals and low frequency portion from the x-ray beam, high pass filtering the detected x-ray signals to obtain a spatial spectral estimate of the high frequency portion, and using demodulation to effectively shift the high frequency portion to low spatial frequencies. The shifted low spatial frequency signals are then weighted to provide an estimate of the low frequency content of the detected unmodulated x-ray signals without scatter. The estimated low frequency content is then subtracted from the earlier spectral estimate of the combined scatter x-ray signals and the low frequency portion from the x-ray beam. An inverse Fourier transform of the estimated low frequency content provides an estimate of the scatter signal in k-space.

In a preferred embodiment, the x-ray beam is amplitude modulated by using a calibration sheet having spatially variant attenuation material between the x-ray source and the object to be imaged, thereby amplitude modulating the primary distribution and make scatter signal and primary signal distribution strongly separate in the Fourier domain or k-space.

In effect, the amplitude modulation creates a side band with frequency equal to the sum of the x-ray frequency and modulation frequency which translates the detected signal to higher frequencies in k-space and away from the lower frequency scatter. The modulated signal is high pass filtered to eliminate low frequency scatter, and then the high pass filtered signal is low pass filtered or demodulated to recover the low frequencies of the primary signal.

The invention and object and features thereof will be more readily apparent from the following detailed description and appended claims when taken with the drawings.

BRIEF DESCRIPTION OF THE DRAWINGS

FIG. 11 illustrates the errors in the scatter corrected images of line integrals (after the log operation), using different schemes.

FIGS. 12A, 12B illustrate scatter corrected images using primary modulation, but without boundary detection. Display window: [−200 500]HU.

DETAILED DESCRIPTION OF ILLUSTRATIVE EMBODIMENTS

The invention obtains a measure of image signal from scatter radiation by first detecting signal with combined scatter signal and low frequency signal from primary radiation, and then using modulation techniques to obtain a measure of low frequency signal from the primary radiation which is subtracted from the detected combined signal to isolate the scatter signal.

We insert a calibration sheet with spatially variant attenuating materials between the x-ray source and the object to modulate the primary distribution and make scatter and primary distributions strongly separate in the Fourier domain. With subsequent image processing techniques, the scatter distribution of the modified x-ray system is estimated accurately and artifacts are substantially reduced in the reconstructed images. This method provides scatter correction using a single scan acquisition without the loss of realtime imaging capability. The concept of "primary modulation" makes this method distinct from the current scatter correction methods, and provides advantages in implementation as well as high scatter estimation accuracy.

We will describe the system geometry and the scatter correction algorithm; the key hypothesis that the high frequency components of the x-ray source distribution do not result in strong high-frequency signals in the scatter distribution is validated using MC simulations; then we evaluate the performance of the correction method using MC simulations on a software humanoid phantom, and preliminary physical experiments are carried out on our table-top CBCT system to provide an experimental verification of the algorithm.

The methodology of scatter correction using primary modulation is first presented in a heuristic manner. Assumptions are made in the development of the algorithm, and their accuracy will be validated by MC simulations. The evaluation of the algorithm will be presented later in discussing experiment results.

Concept of Primary Modulation

Figure 1:
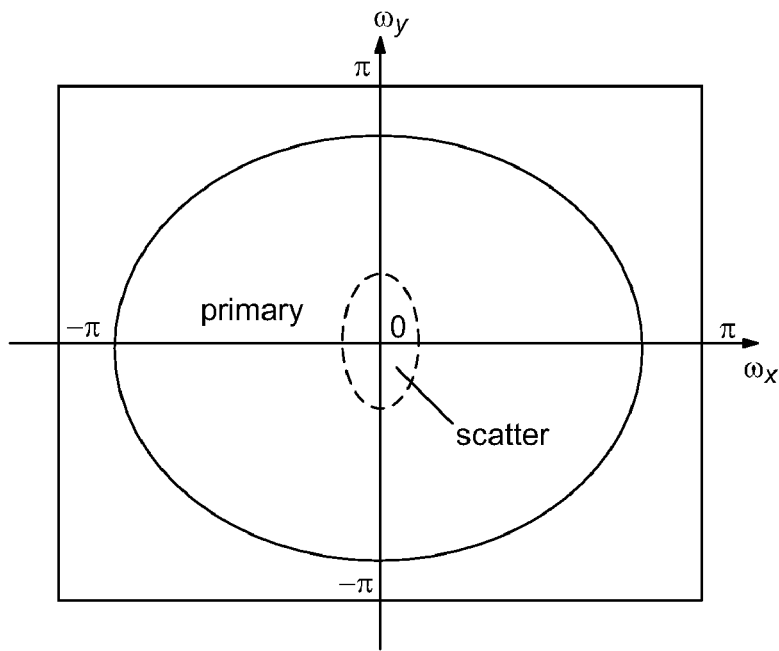
FIG. 1 is a conceptual illustration of typical primary and scatter distributions in the Fourier domain, before correction.

In the absence of scatter correction, FIG. 1 conceptually depicts the regions in the Fourier domain where the main energy of the scatter and primary distributions of one x-ray projection is located. The contribution of Rayleigh scattering is small in the scatter distribution. If only Compton scatter is considered, low-frequency components dominate in the scatter distribution, while the primary distribution, closely related to the object, is more arbitrary but still has strong low-frequency components. The supports of the scatter and primary distributions overlap completely, while a fraction of Fourier space is left almost blank. From an information channel point of view, a better use of this "channel" would be reallocating the primary and scatter distributions such that more primary resides in the region of Fourier space where there is no or less scatter ("water-filling" scheme as in information theory).

Manipulating the scatter distribution is difficult because of the complexity in the physics of the scattering process. In fact, we assume that adding high-frequency components in the x-ray source distribution does not result in strong high frequency components in the scatter, even though it might change the low-frequency content. By contrast, if the beam hardening effects are negligible, the detected primary distribution is linearly proportional to the incident x-ray distribution. Therefore, an x-ray source distribution with high-frequency components is able to "code the primary" before projection. Equivalently, the original primary distribution acquired using a uniform x-ray source distribution is partially modulated by a high-frequency function defined by the new x-ray source distribution, while the scatter distribution is still predominantly low-frequency due to the hypothesis. The information content of the modulated primary distribution reaches the detector without much contamination of scatter, and the scatter distribution can therefore be estimated and corrected. The hypothesis relating to the scatter is the key to the algorithm development.

Figure 2:
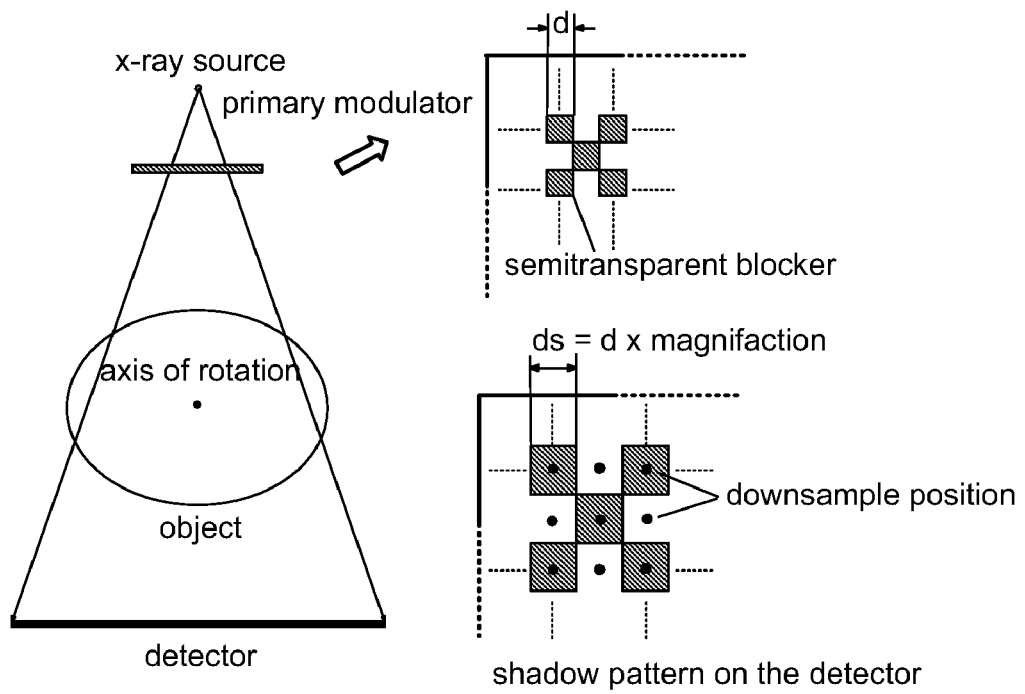
FIG. 2 illustrates a geometric configuration of the x-ray system with the insertion of the primary modulator.

One easy way to alter the incident x-ray spatial intensity distribution is to insert between the x-ray source and the object a calibration sheet with attenuating materials—a "primary modulator". In order to introduce high-frequency components, in one embodiment the primary modulator consists of semi-transparent blockers that are arranged in a "checkerboard" pattern, i.e., semitransparent and "transparent" blockers alternate. Other geometries could be used in the modulator. FIG. 2 shows the system geometry with the insertion of the primary modulator. Based on the main idea presented above, scatter correction of this modified imaging system can be implemented. Note that all of the data analysis and processing are done before the log operation on the projection data that calculates the images of the attenuation coefficient integrals along the projection lines (referred to as line integral images hereafter), and the images are processed independently for each projection angle during the data acquisition of rotation.

To avoid the edge effect of the blocker shadows, only the data at the centers of high and low intensity regions on the detector are used in the scatter estimation and correction, i.e., the projection image is downsampled with a sampling period equal to the diameter of the blocker shadow (see FIG. 2). Parameters i and j are the horizontal and vertical indices of the downsampled data, and p' and p are the downsampled primary distributions with and without the primary modulator. Denoting the photon transmission of the semi-transparent blockers as $\alpha$, we have:

$$p'(i, j) = \begin{cases} p(i, j), & \text{if } (i+j) \text{ is even,} \\ \alpha p(i, j), & \text{if } (i+j) \text{ is odd.} \end{cases} \quad (1)$$

$$\Rightarrow p'(i, j) = p(i, j)\frac{1+\alpha}{2} + p(i, j)\frac{1-\alpha}{2}(-1)^{(i+j)}$$

Denote P and P' as the discrete Fourier transform (DFT) of p and p', respectively, and $(\omega_x; \omega_y)$ as the coordinate system in the Fourier domain. Taking the DFT of both sides of equation (1), one obtains:

$$P'(\omega_x, \omega_y) = P(\omega_x, \omega_y)\frac{1+\alpha}{2} + \quad (2)$$

$$P(\omega_x - \pi, \omega_y - \pi)\frac{1-\alpha}{2}\omega_x, \omega_y \in [-\pi, \pi]$$

The above equation shows that part of the primary is replicated (modulated) to the high-frequency region in Fourier space, with weighting $$\frac{1-\alpha}{1+\alpha}.$$

Notice, on the other hand, that if α is not very small, i.e., the high-frequency components of the incident x-ray spatial distribution are not strong, low frequencies still dominate in the scatter distribution, due to the hypothesis discussed above.

Figure 3:
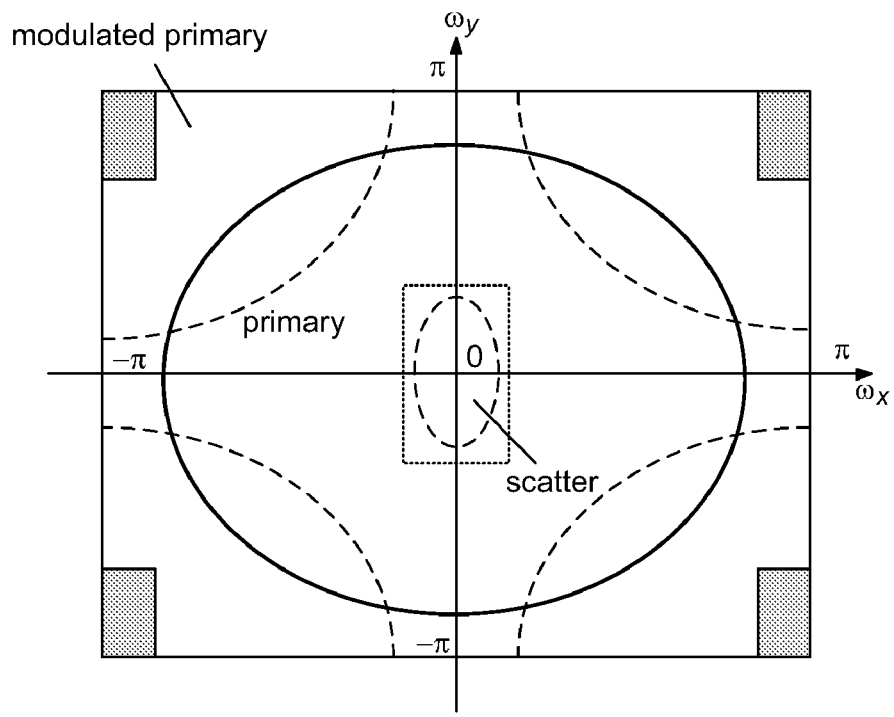
FIG. 3 is a conceptual illustration of the primary and scatter distributions in the Fourier domain, with the primary modulator in place.

With the primary modulator in place, the Fourier domain distributions of primary and scatter are shown in FIG. 3. Now, the primary is more separately distributed, and it provides a possibility for accurate scatter estimation. Since the low-frequency region is the only region where primary and scatter distributions are overlapping, knowledge of the low-frequency components of the primary P' (encompassed by the dotted line around the origin) suffices to extract the scatter distribution, while the low-frequency primary can be estimated from its replica in the high-frequency region (shaded area).

The estimation accuracy of the low-frequency primary spatial spectrum from the high-frequency components is crucial in this approach. The Fourier domain distribution of the projection image before modulation (solid line in FIG. 3) should not heavily contaminate the region of high-pass filtering (shaded area in FIG. 3). Otherwise, the high-frequency spectrum of the initial projection is demodulated together with the modulated low-frequency spectrum, making the low-frequency primary estimation inaccurate. This requires that: 1) the initial primary before modulation does not have large high-frequency components; or, 2) the modulation frequency is high relative to the major frequency content of the primary, and modulation weight $$\frac{1-\alpha}{1+\alpha}$$

is large. The latter requires careful choice of the system parameters, while the former can be improved by preprocessing techniques on the projection images.

Auxiliary Boundary Detection

As discussed above, the algorithm will generate relatively large scatter estimation error in those regions of image that have large high-frequency components. In the projection images before the log operation, most of the high-frequency components of the primary distribution result from the sharp transitions at the object boundaries. Since linear filtering techniques are used in the data processing, the resulting error in the scatter corrected reconstructed images not only resides at the object boundary but also spills into the inside of the object where the reconstruction is more sensitive to scatter estimation error due to the small primary signal. An auxiliary boundary detection algorithm is therefore introduced to improve the scatter correction. The main idea is to pre-multiply the initial scatter-plus-primary projections by a 2D boundary profile function T, to smooth out the sharp transitions at the edges of the object. The boundary profile function smoothly decreases from 1 to a small value around the boundaries going from the interior towards the exterior of the projection of the object, with the sharpest slope around the object boundary. It would seem reasonable to divide the calculated scatter estimate by T to reverse the effect of pre-multiplication. However, based on experimental results, we found that the estimation error is boosted by the division by T, where the value of T is small; on the other hand, the large value of the primary outside the boundary makes the scatter estimation there less demanding. Therefore, the division step is omitted in the implementation.

The boundary profile function T depicts the shape of the object boundary on the projection image. The estimation of this function, in general, is complicated, especially without prior information of the object. Fortunately, the objects scanned in a clinical setting usually have simple quasi-cylindrical or quasi-ellipsoidal shapes. The boundary profile can therefore be estimated based on the first order derivative of the projection image. A 2D Gaussian filter is then applied to smooth the transition.

Note that the boundary detection is not crucial to the overall algorithm performance, especially when system parameters are chosen to accommodate more primary high-frequency components in the scatter estimation. From physical experiments, we also found that a very rough estimation of the boundary profile is sufficient to improve the image quality. Although the simple derivative-based estimation is error-prone in the presence of noise, the scatter correction algorithm is still stable.

The Soft Cutoff Function

Figure 4:
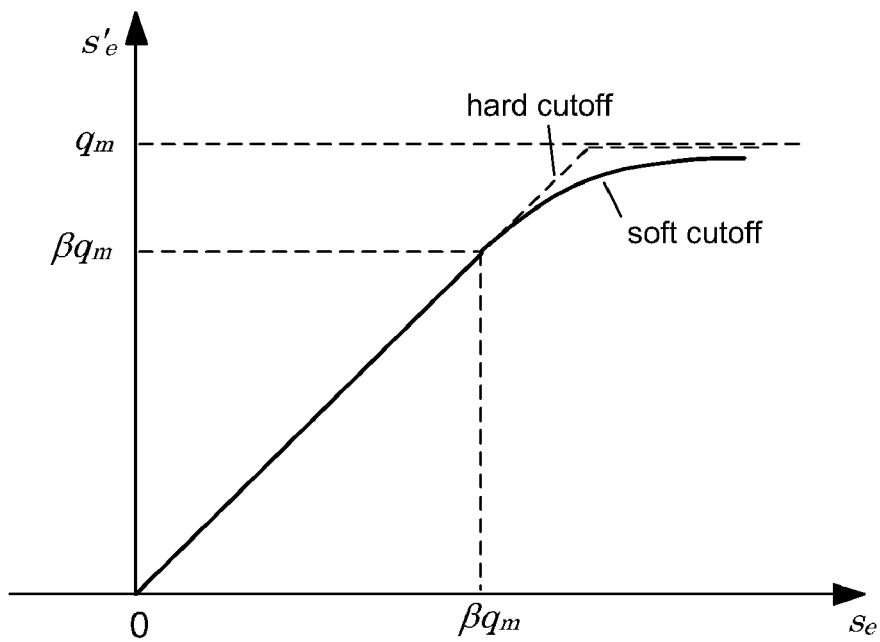
FIG. 4 illustrates the cutoff functions.

A second issue of importance to the scatter correction algorithm is the subtraction of the estimated scatter from the measured projection data. The log operation that follows implicitly requires that the estimated primary be positive. A cutoff function, therefore, is needed to guarantee that the estimated scatter is always less than the measured projection data. FIG. 4 shows the cutoff functions. The abrupt transition of a hard cutoff function with simple thresholding results in streaking artifacts, especially when the scatter estimation is inaccurate. To make the scatter correction algorithm more tolerant to estimation error, a smooth soft cutoff function is used with an exponential function to smooth the transition. The exponent is chosen to make the first order derivative continuous.

Denote $q_m$ as the measured projection data, $s_e$ as the estimated scatter, and $s'_e$ as the value that will be subtracted from $q_m$. The relationship between $s_e$ and $s'_e$ is defined by the soft cutoff function as:

$$s'_e = \begin{cases} 0, & s_e \leq 0, \\ s_e, & 0 < s_e < \beta q_m, \\ q_m + (\beta-1)q_m e^{-\frac{s_e - \beta q_m}{(1-\beta)q_m}}, & s_e \geq \beta q_m. \end{cases} \quad (3)$$

where the parameter $\beta \in (0; 1)$, and is chosen empirically. If the scatter estimation is accurate, a large β can be used; otherwise, a small β should be chosen to suppress the overshoot error when the scatter estimate is inaccurate and very large.

The Scatter Correction Algorithm

With the primary modulator in place, an efficient scatter correction can be obtained for this modified system. All of the above observations lead to the following steps for the new scatter correction algorithm, which can be embedded in the image processing stage of conventional x-ray CT:

Step 1 Do two pre-scans with and without the primary modulator, with no object, to obtain an estimate of the blocker shadow position on the detector and the blocker transmission α.

Step 2 Acquire projection images of the object with the primary modulator in place.

Step 3 For each projection image (could be processed in parallel with step 2):

Step 3.1 estimate the boundary profile T using the auxiliary boundary detection algorithm (in the estimation, use the pre-scan result to cancel the effect of the blockers on the projection image), multiply the projection image by T;

Step 3.2 downsample the image at the centers of the blocker shadows;

Step 3.3 low-pass filter the downsampled image to obtain an estimate of scatter plus low-frequency primary;

Step 3.4 estimate the high-frequency components of the modulated primary by high-pass filtering the initial downsampled projection (the high-pass filter has the same size of support as the low-pass filter in step 3.3), then demodulate to the low-frequency signal, and weight it by $$\frac{1-\alpha}{1+\alpha};$$

this provides an estimate of low-frequency primary;

Step 3.5 subtract the result obtained in step 3.4 from that in step 3.3;

Step 3.6 upsample to obtain a scatter estimate of the whole field, apply the soft cutoff function.

Step 3.7 subtract the scatter estimate from the initial projection image to obtain a primary estimate, and divide the result by the flat field distribution with primary modulator in place that is measured in the pre-scan. Take the negative log value.

Step 4 Reconstruct the object using the processed projection images.

(The Fourier domain illustration of steps 3.3-3.5 is shown in FIG. 3.)

Choice of System Parameters

While the boundary detection and the soft cutoff function improve the scatter correction, algorithm performance is mainly determined by the choice of system parameters. Recall that for improved scatter estimation, contamination of the high-pass filtering region in step 3.4 by the unmodulated initial primary distribution should be minimized. Based on this, the choice of proper system parameters is discussed below, although the optimal values are still to be determined by simulations and/or physical experiments.

1) Blocker Size d: The blocker size d determines the pitch of the data samples that are used in the scatter correction, and hence the primary modulation frequency. To make the modulated and unmodulated primaries strongly separate, a small d is preferred. On the other hand, in a practical CT system, d can not be too small because of the penumbra effects from the finite size of the x-ray focal spot.

2) Blocker Transmission a: With the primary modulator in place, the ratio of modulated primary to unmodulated primary is $$\frac{1-\alpha}{1+\alpha}.$$

A smaller α is needed for a larger primary modulation, and therefore a better scatter correction. However, decreasing α, or increasing the blocker attenuation also results in stronger high-frequency components in the primary, which would increase the high-frequency components in the scatter and therefore might undermine the critical assumption that the scatter profile is still dominated by low-frequency components even if a calibration sheet of high-frequency modulation is inserted.

3) Cutoff frequency of the low-pass filter $\omega_{max}$: (The cutoff frequency of the high-pass filter is $\pi-\omega_{max}$.) $\omega_{max}$ is mainly determined by the scatter distribution. It should be chosen large enough to cover most of the scatter Fourier domain expansion, although a large $\omega_{max}$ also increases the risk that unmodulated high-frequency primary is demodulated back as an estimate of low-frequency primary. To make the algorithm more general, we use the same $\omega_{max}$ for the two orthogonal directions of the 2D image. However, a combination of $\omega_{max}$ values for different directions could be used in the algorithm, as long as the support of the low-frequency filter and its corresponding high-frequency filter does not have joint areas.

The choice of the system parameters is a trade-off among many factors. From a practical point of view, the blocker size and transmission deserve more consideration since they are hardware related and usually cannot be easily changed. We use simulations to find proper value ranges, with further refinement to be provided by physical experiments.

Hypothesis of Scatter Distribution

The key hypothesis in the primary modulation method is that the high-frequency components of the x-ray spatial distribution do not result in strong high-frequency signals in the scatter. In other words, for the algorithm to work, low-frequency changes in the scatter after the insertion of the modulator are acceptable, but the insertion should not introduce much high-frequency signal in the scatter. This assumed property enables the primary to be manipulated without significantly expanding the scatter spatial spectrum in the Fourier domain, and makes the separation of primary and scatter possible.

X-ray scattering is a stochastic multi-interaction process that is dependent on the imaging geometry and the object, and an analytical validation of the main hypothesis of this algorithm is complicated. A MC simulation is therefore used to provide justification.

However, two additional arguments support the hypothesis. Because scattering is a random process that removes the spatial information from the initial signal, therefore the high frequency content of the incident x-ray source distribution will be lost during the scattering process. The hypothesis could also be explained by the simplified analytical models of scattering as used in many convolution based scatter estimation algorithms. A typical example is where the point spread function (PSF) of the single scatter on a homogeneous object is derived analytically based on the Klein-Nishina formula, which characterizes the behavior of Compton scattering accurately. The resultant equation is a function of object thickness, object-to-detector distance (air gap), and the linear attenuation coefficients of primary and scattered radiation. The PSF's for different parameter values are typically low-frequency responses. As the object thickness and air gap increase, the PSF becomes smoother and wider, i.e., more constrained to low frequencies. Since multiple scatter can be considered as consecutive single scatters, it is expected to have more low frequency components in its PSF. Therefore, we can conclude that Compton scattering has a low-frequency response to the x-ray source distribution. Since Rayleigh scatter consists mostly of small angle scattering, its contribution has high-frequency components. However, the contribution of Rayleigh scatter is considerably smaller than that of Compton scatter, and it does not degrade the effectiveness of the proposed scatter correction algorithm, as will be shown with simulated and measured data below.

MC Validation of the Key Hypothesis

The MC simulations were carried out using Geant4 MC software. The implementation of the code was verified by comparison with the SIERRA MC code for several simple geometries.

Figure 5:
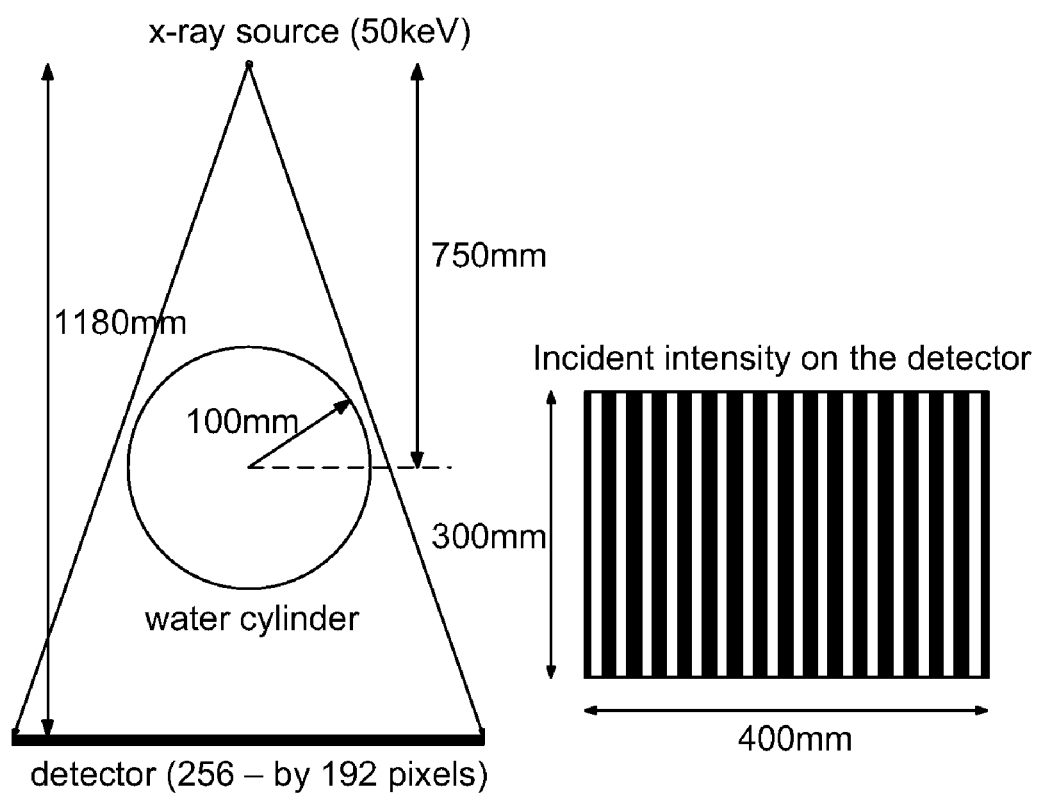
FIG. 5 illustrates the simulation setup for the validation of the key hypothesis.

FIG. 5 shows the simulation setup. We chose parameters of system geometry that are typical for C-arm CT. The MC simulation is time-consuming and the simulation time is proportional to the total number of incident photons; on the other hand, generating a scatter distribution with good quantum noise statistics requires a large number of incident photons per ray. To save computation, we used a relatively large pixel diameter on the detector, 1:56 mm. Two simulations were done to investigate the sensitivity of scatter to the spatial variation of the incident photon intensity. The first simulation used a uniform intensity distribution, with 3,100,000 photons per ray. The second used a distribution as shown in FIG. 5. The detector was divided into strips, and every other strip had no incident photons. This represents the maximum high-frequency content that could be added into the incident photon intensity distribution, given the spacing of the strips. To avoid losing high-frequency information due to insufficient sampling, the strip width was set to 12:5 mm, or 8 pixels on the detector. The number of photons per ray was doubled to make the total number of incident photons the same. For both simulations, the x-ray source was monochromatic operating at 50 keV. It illuminated only the region of detector, and a uniform water cylinder of diameter 200 mm was used as the object.

Figure 6A:
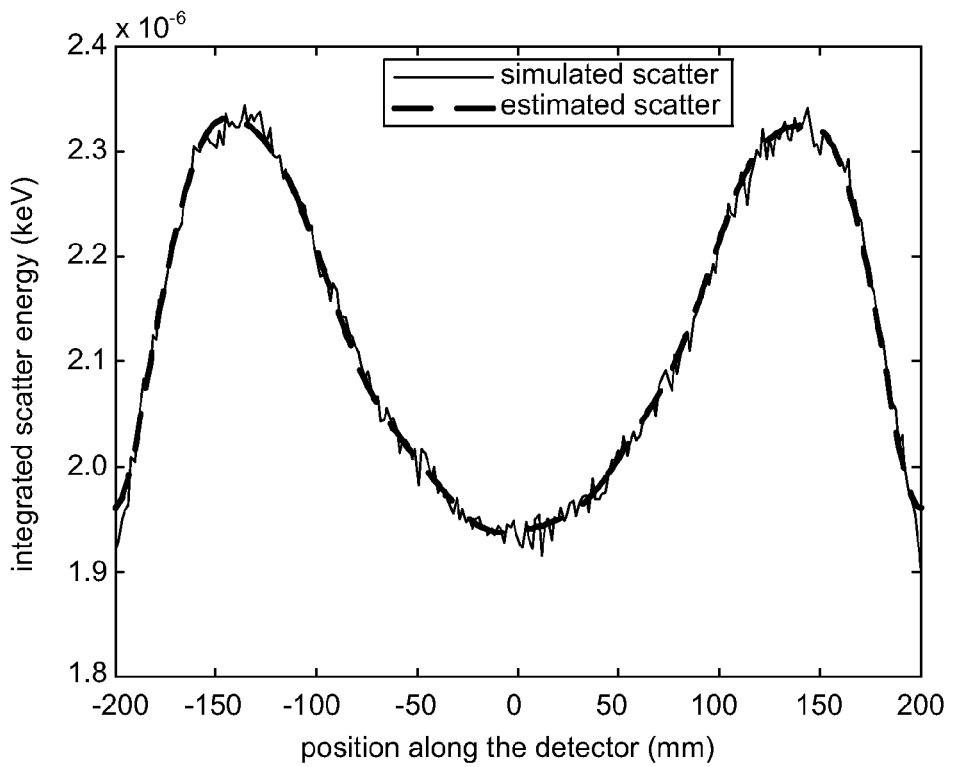
FIGS. 6A, 6B illustrate the central horizontal profiles of the simulated scatter distributions and the estimated scatter distributions.
Figure 6B:
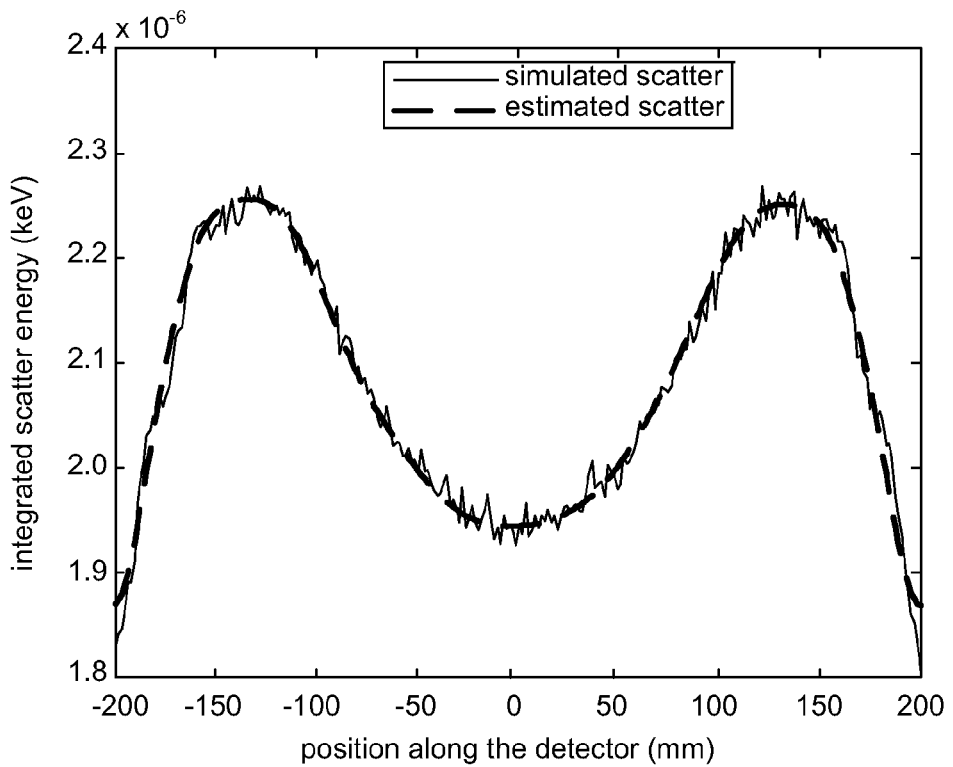

Shown in FIG. 6 are the 1D profiles taken at the central horizontal lines of the simulated scatter distributions (solid lines). The difference of the two scatter distributions could be found mainly around the object boundary (±159:4 mm on the detector), because the object attenuation changes rapidly in this region. The comparison also illustrates, in the second simulation, that although the x-ray source distribution has strong spatial high-frequency components, the resultant scatter distribution still has large low-frequency signals. The disturbance in the scatter due to the non-uniform x-ray distribution contains high frequency components, as well as low-frequency signals that are acceptable in the hypothesis. Although not shown here, a comparison of the scatter profiles from Rayleigh and Compton indicates that most of the high-frequency discrepancy between scatter profiles with and without the strip pattern stems from Rayleigh scattering, which is more closely correlated with incident primary photon distribution due to its narrow PSF. To illustrate the impact of these high-frequency variations on the scatter estimation, the estimated scatter profiles are also shown in FIG. 6 (dashed lines). This data was analyzed using the steps of the proposed algorithm. The scatter was first downsampled at the center of the low and high intensity regions on the detector. To suppress the noise, the downsampled data was taken as the average of the neighboring 4 pixel values. Then a low-pass filtering with the cutoff frequency $$\omega_{max} = \frac{\pi}{2}$$

was performed, and finally, the result was upsampled back to the original length. We focus on the estimation error of the scatter due to the change in the scatter distributions only, and the primary data was not used in the estimation of the scatter. FIG. 6(b) shows that the scatter estimate matches the original scatter distribution, with a relatively larger error at the object boundaries. Note, however, that if a semitransparent strip pattern is used, i.e. high-frequency components in the x-ray source distribution are reduced, the error will be reduced as well and in addition the high primary value will alleviate the impact of the scatter estimation error outside the object boundary.

Figure 7:
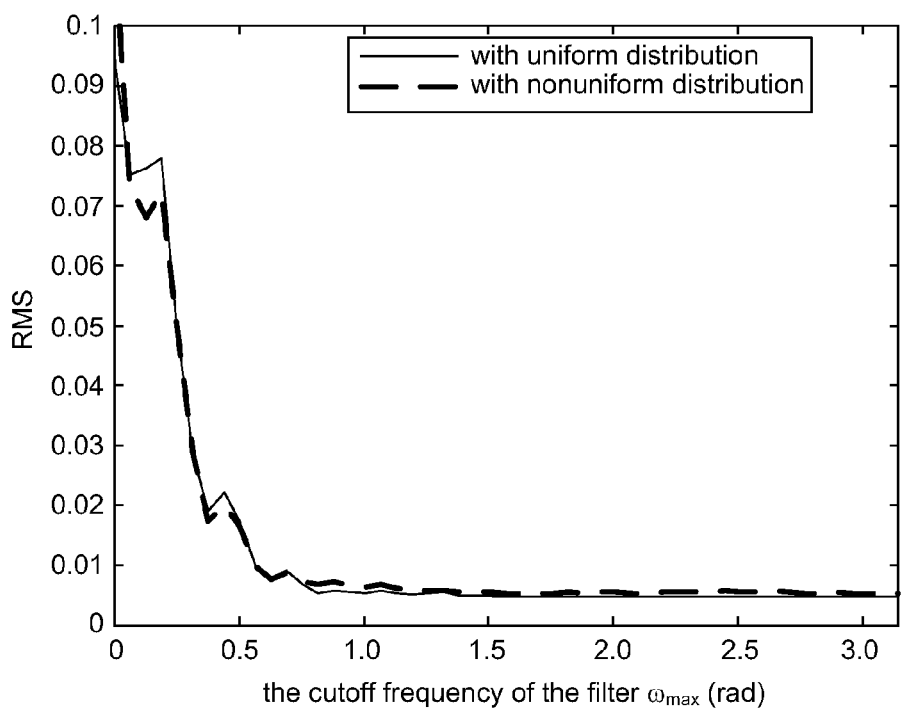
FIG. 7 illustrates the RMS of the relative estimation error inside the object boundary (from −159.4 mm to 159.:4 mm on the detector) for different $\omega_{max}$.

Further verification is provided by examining the root-meansquare's (RMS's) of the estimation error relative to the simulated scatter, calculated for the data inside the object boundary from −159:4 mm to 159:4 mm on the detector. The RMS's of FIGS. 6(a) and 6(b) are 0.48% and 0.54%, respectively. The results for different $\omega_{max}$ used in the low-pass filtering are shown in FIG. 7. Small difference is found for the two different x-ray source distributions. When $$\omega_{max} > \frac{\pi}{4},$$

both distributions result in the RMS of the relative error less than 0.8%. These results indicate that although high-frequency variation exists in the scatter distribution when the high-frequency components are present in the x-ray source distribution, the resultant error in the scatter estimation using low-passing filtering is small. In other words, the low-frequency signals still dominate in the scatter distribution.

Scatter Correction Experiments

Both simulation and physical experiments are carried out to fully evaluate the performance of the algorithm. Since the goal of this study is to develop an effective scatter correction technique for clinical use, especially when scatter-to-primary ratio (SPR) and its variation are both very high, simulations of chest imaging with a humanoid software phantom are used to investigate the effect of the choice of the algorithm parameters on the reconstructed image quality, and to suggest proper parameter values. Physical experiments on a standard evaluation phantom also provides a solid validation of the algorithm in a practical environment.

Algorithm Implementation Details

Several details must be considered for a practical implementation of the algorithm.

In the MC simulations, the knowledge of the blocker pattern was assumed. In the physical experiments, the blocker transmission and the sampling rate were estimated using the pre-scans (step 1). We determined the centers of the blocker shadows by maximizing the correlation between the flat field image of the modulator and a grid function.

In step 3.1, the boundary was estimated line by line along the direction parallel to the plane of the source trajectory. We took the first derivative of the projection image along that line, and then found the positions where the derivatives were the most positive and the most negative. This gives a rough estimate of the object boundary. We assigned 1 to the pixels within the boundary and 0.01 outside. Finally, a 2D Gaussian filter was applied to the 2D profile. The standard deviation of the Gaussian kernel was chosen empirically. From experiments, we found that the value could range within 5%~20% of the coverage of the object on the detector in the horizontal direction, and the scatter estimation error was insensitive to the choice. A constant standard deviation, 40 mm, was used for all the simulations and for the physical experiments. The above algorithm works for quasi-cylindrical objects as were used in this paper. For other types of objects, the algorithm could be developed similarly.

To make the algorithm more robust to noise, in step 3.2, the downsampled data was the average of a small neighborhood (less than the blocker shadow size) around the sample point. The simulation experiments were noise-free, and downsampling without averaging was used; in the physical experiments, we averaged an area of 10-by-10 pixels on the detector.

Filtering techniques were used in several steps of the algorithm (step 3.3 and step 3.4), including the upsampling step (step 3.6). To suppress the error from filtering a finite length signal, we applied Hamming windows on the filters with the same width, and the images were zero-padded to twice signal length along both axes. To make the algorithm more general, we chose the same cutoff frequency $\omega_{max}$ in the two orthogonal directions of the image.

We used $\beta=0:99$ in the soft cutoff function of step 3.6.

Simulation Experiments

Figure 8:
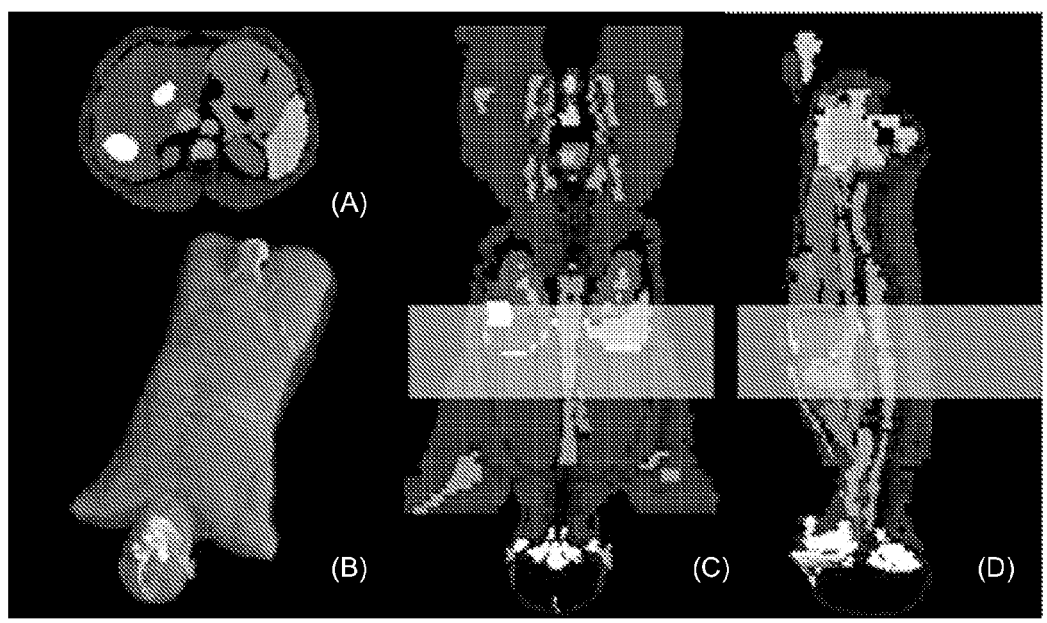
FIG. 8 illustrates the Zubal phantom. a) 3D view; b) axial view; c) coronal view; d) sagittal view.

1) The Zubal phantom and MC simulation: The Zubal phantom [27] was used in the simulation experiments, shown in FIG. 8. It is a humanoid software phantom from head to hip, with total size 128-by-128-by-243 and 4 mm resolution. The simulation and reconstruction parameters are summarized in Table. I.

TABLE I

PARAMETERS OF THE SIMULATION EXPERIMENTS

| Imaging parameters: | |
| --- | --- |
| x-ray source | monochromatic, 50 keV |
| source to detector distance | 1180 mm |
| source to rotation axis distance | 750 mm |
| detector size | 770 mm-by-385 mm |
| | 1024-by-512 pixels |
| rotation | circular, 360 deg |
| number of views | 360 |
| Reconstruction parameters: | |
| reconstructed voxel size | 0.781 mm in all directions |
| reconstructed volume size | 512-by-512-by-64 voxels |
| algorithm | FDK |

Note that a large detector was used to avoid truncation of the projection images, and therefore the scatter was exaggerated as compared to a practical implementation of the CBCT system. The x-ray source was monochromatic, so that the reconstructed images are free of beam hardening artifacts. The standard FDK algorithm was used for the reconstruction.

We chose to do a chest scan (see FIG. 8), since in the lung region, the high SPR and SPR variation make scatter correction more challenging. The plane of the source trajectory was on slice 108 of the phantom. The scatter distributions were generated using the Geant4 MC software. Since generating noiseless scatter distributions using MC simulation is very time-consuming, the Richardson-Lucy (RL) fitting algorithm was used such that accurate and noiseless scatter distributions could be obtained using a much smaller number of photons. The acceleration of the MC simulation by this algorithm stems from the fact that scatter distributions are very smooth (low-frequency), so the high-frequency statistical noise in the simulation of relatively few photons can be removed after curve fitting. The primary projections were calculated separately using line integration and weighted to match the SPR. Denoting S and P as the scatter and primary distributions obtained from MC simulation, $S_{RL}$ as the scatter distribution after $R_L$ fitting, and $P_{LI}$ as the primary distribution by line integral calculation, the weight factor K on $P_{LI}$ for each projection is computed as follows:

$$\frac{K\sum P_{LI}(i,j)}{\sum S_{RL}(i,j)} = \frac{\sum P(i,j)}{\sum S(i,j)} \quad (4)$$

$$\Rightarrow K = \frac{\sum S_{RL}(i,j) \sum P(i,j)}{\sum P_{LI}(i,j) \sum S(i,j)}$$

Even with the acceleration, MC simulations are still computationally intense. For the purposes of saving computation, we assumed that the error in the scatter estimation due to the insertion of the primary modulation was small (supported by the MC simulations in Section III), and the same scatter distributions obtained without the modulator were used for the simulations. In the implementation of the primary modulation method, a perfect knowledge of the blocker shadow position was also assumed. The simulations do not include quantum noise; the effect of noise is addressed in the physical experiments.

2) Determination of the Reconstruction Accuracy: Side-by-side image comparisons are used to show the improvement of reconstruction accuracy using our scatter correction approach. In addition, the relative reconstruction error (RRE) is also used as a quantitative measure. Denoting the reconstructed image with scatter correction as V, and the ideal reconstruction without scatter as $V_0$, the RRE is defined as relative mean square error of the reconstructed images in the region of interest (ROI):

$$RRE = 100\% \sqrt{\text{mean}\left[\left(\frac{V(x,y,z) - V_0(x,y,z)}{V_0(x,y,z)}\right)^2\right]}, \quad (5)$$

$(x,y,z) \in ROI$ where (x; y; z) are the coordinates of the reconstructed image. The ROI is chosen as the central reconstructed volume of size 128-by-128-by-64. Parameters V and V0 are in Hounsfield units (HU). To make the reconstruction linear rather than affine, the value is shifted by 1000 in the RRE calculation, such that air is 0 HU and water is 1000 HU.

Figure 9A:
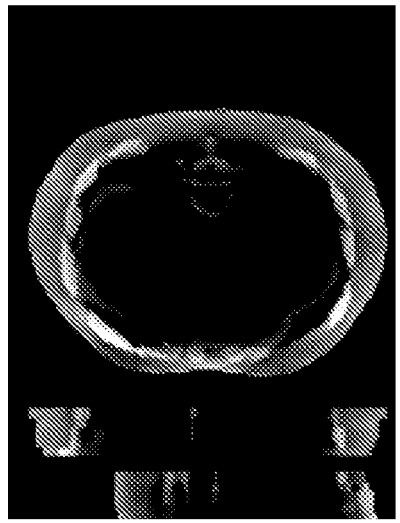
FIGS. 9A-9D illustrate the axial, coronal and sagittal views of the reconstructed volumes, without scatter correction and with scatter corrected by different methods.
Figure 9B:
Figure 9C:
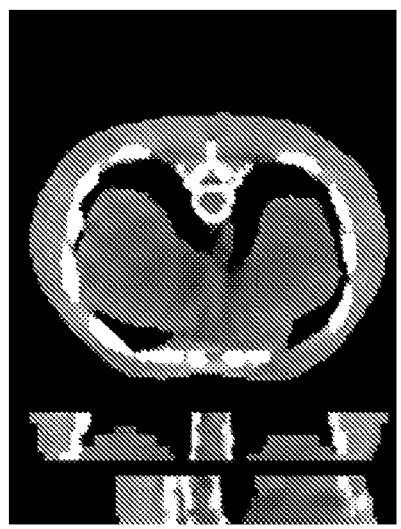
Figure 9D:
Figure 10A:
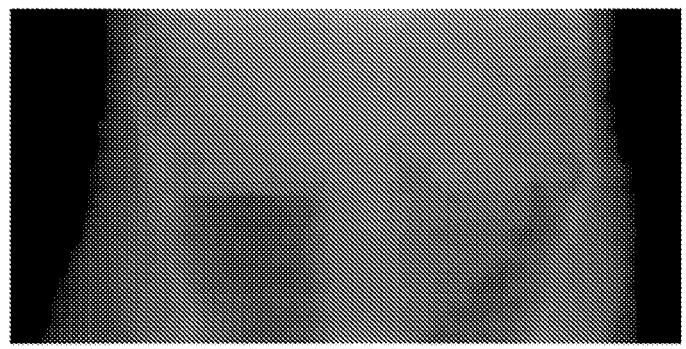
FIGS. 10A-10D illustrate the line integral images (after the log operation) with and without scatter correction using primary modulation, and difference images calculated relative to the scatter free images.
Figure 10B:
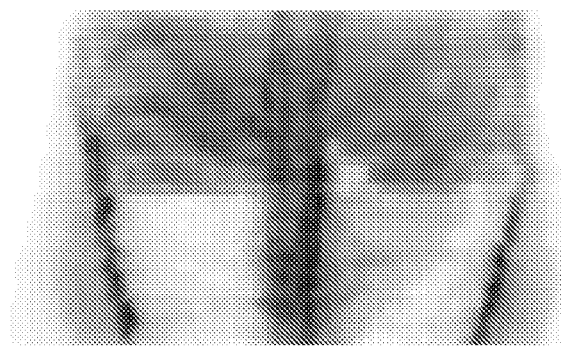
Figure 10C:
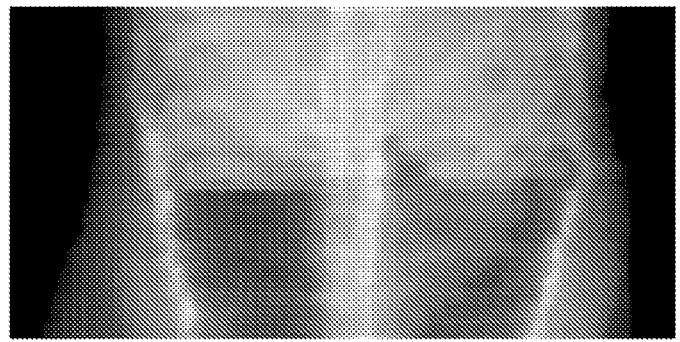
Figure 10D:
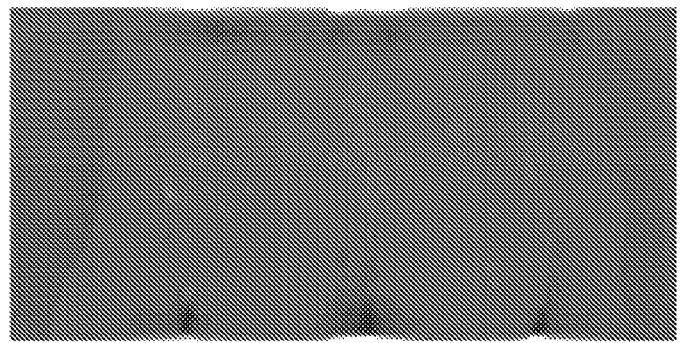
Figure 13A:
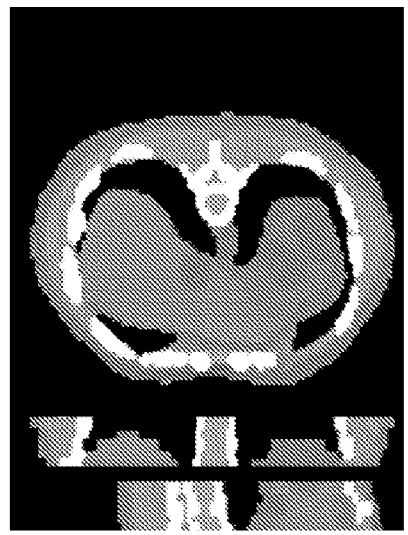
FIGS. 13A-13D illustrate representative reconstructed images with the scatter correction using primary modulation.
Figure 13B:
Figure 13C:
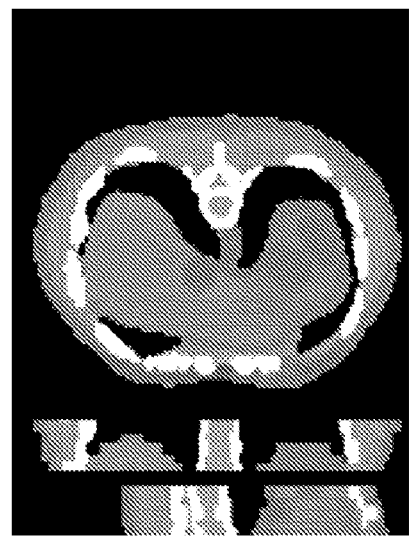
Figure 13D:
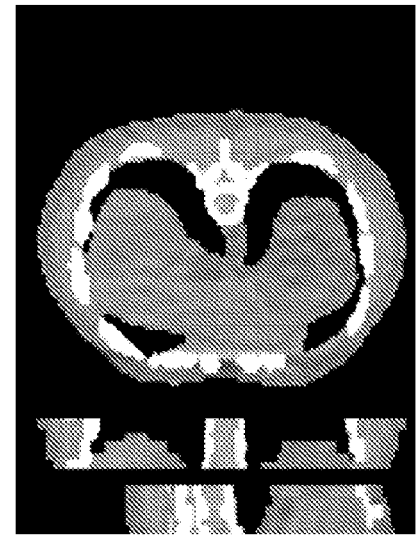

3) Reconstruction Without Scatter Correction and With Scatter Corrected By Other Methods: FIG. 9 shows the challenge of effective scatter correction. FIG. 9(a) is reconstructed without scatter correction. The cupping and shading artifacts caused by scatter are very severe in the image, and the RRE is 74.2%. We also estimate the scatter by a pre-scan on an all-water phantom with the same boundary, assuming the boundary of the object is known. The scatter artifacts are reduced slightly, but the overall image quality is still poor (FIG. 9(b)). Image corruption is also found in FIG. 9(c), where an anti-scatter grid is used to suppress the SPR. The primary and scatter transmissions of the grid are 64.2% and 6.3%, respectively, based on the technical data of the Siemens 12/40 type anti-scatter grid for fluoroscopy imaging. The simulation uses a simple scaling on the scatter and primary. As a reference, FIG. 9(d) is the reconstruction with perfect scatter correction.

4) Reconstruction With Scatter Correction Using Primary Modulation: The scatter correction algorithm by primary modulation contains three parameters: the blocker size d, the blocker transmission α and the cutoff frequency of the low-pass filter $\omega_{max}$. For simplicity, in the simulation results FIGS. 10-15, we use the blocker shadow size ds on the detector in mm or detector pixels as a system parameter instead of the actual blocker size.

The effect of the scatter correction in the projection space is demonstrated in FIG. 10, where the images after the log operation are shown. The difference images are calculated relative to the scatter-free images. FIG. 11 compares 1D profiles taken at the central horizontal lines on the projection data with the same view angle. To illustrate the effect of the boundary detection algorithm, different schemes are used in the scatter correction: without boundary detection, with boundary detection and division by the boundary profile T, and with boundary detection but the division step is omitted. Since linear filtering techniques are involved in the algorithm, if the boundary detection is not used, high-frequency errors that originate from the object boundary have a global effect on the estimated projection image. The line integral images are more sensitive to estimation errors where the primary is low, due to the log operation, and therefore, high-frequency errors appear in the middle of the profile, as shown in FIG. 11. As a result, the reconstructed image has high-frequency artifacts, typically ripples, around the object center. FIG. 11 indicates that the boundary detection algorithm is able to suppress these high-frequency errors effectively, at the price of estimation accuracy loss at the object boundary. Since the ROI is usually the interior of the object rather than the periphery, we use the boundary detection as a supplementary step in the algorithm. Our algorithm only includes the multiplication of the boundary profile T which suppresses the sharp transitions of the boundary on the projection image. The overshoot error caused by the division by T as the final step is also clearly shown in FIG. 11, therefore this step is omitted in the algorithm.

FIG. 12 shows the ripple effect that occurs in reconstructed images when no boundary detection is applied. The same sets of parameters were used as in FIGS. 13(b) and 13(c), which are the scatter corrected images with the boundary detection. The comparison shows that more pronounced high-frequency artifacts are present in FIG. 12.

Figure 14A:
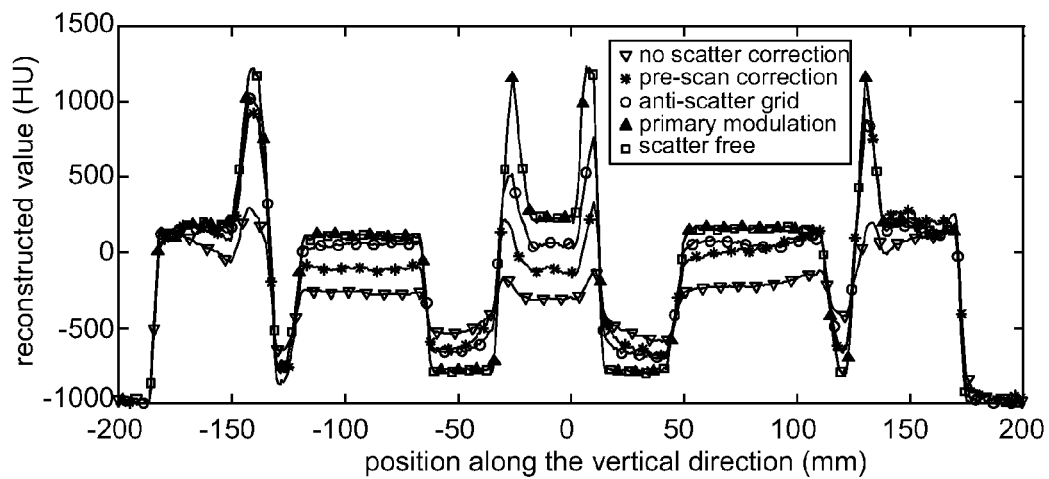
FIGS. 14A, 14B illustrate the 1D profiles of different reconstructed images and the differences calculated relative to the scatter free reconstruction.
Figure 14B:
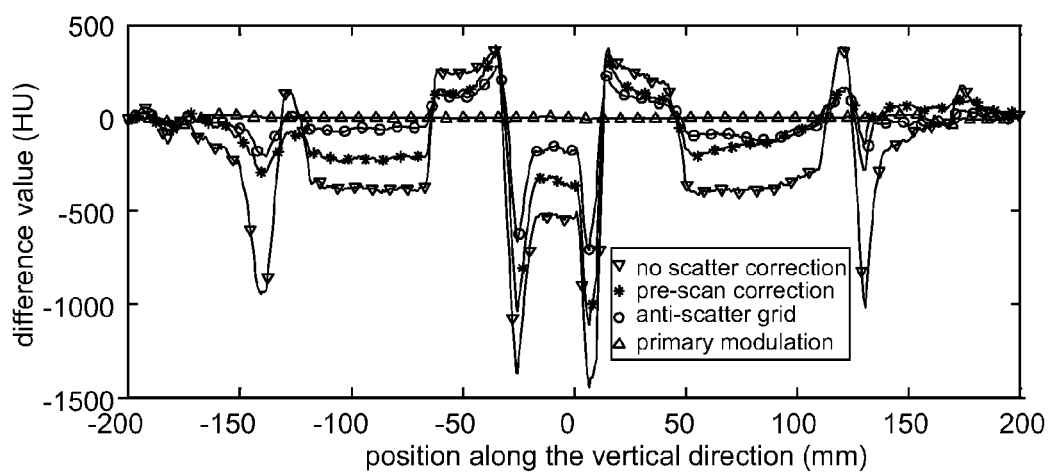

Representative reconstructed images with scatter corrected using the proposed algorithm with different system parameters are shown in FIG. 13. With proper parameter values, the scatter artifacts are significantly suppressed, and the RRE value can be reduced to less than 1%. FIG. 14 compares the 1D profiles of FIG. 9 and the scatter correction result of FIG. 13(b). The profiles are taken at the central vertical lines of the axial views. The comparison reveals that the scatter correction is accurate in most of the area, with a small error mainly located around the object boundary, due to the imperfection of the boundary detection.

To investigate the effects of the system parameters on the algorithm performance, simulations were also done with various sets of the parameter values. The RRE values of these simulations are summarized in FIG. 15, and the results illustrate the effects of the system parameters as we discussed in Section II-E. If the position of the primary modulator is fixed, the blocker size d can be calculated simply by dividing the corresponding ds by the magnification factor from the primary modulator to the detector. Decreasing d or α increases the scatter correction accuracy, since a higher sampling rate and a stronger modulation make scatter and primary more separable in the Fourier domain. The choice of $\omega_{max}$ should be case-dependent. When the small d or α is chosen to provide accurate scatter correction, a large $\omega_{max}$ should be used; while if the ability of scatter correction is limited by the large d or α, then $\omega_{max}$ should be chosen more conservatively.

Figure 15A:
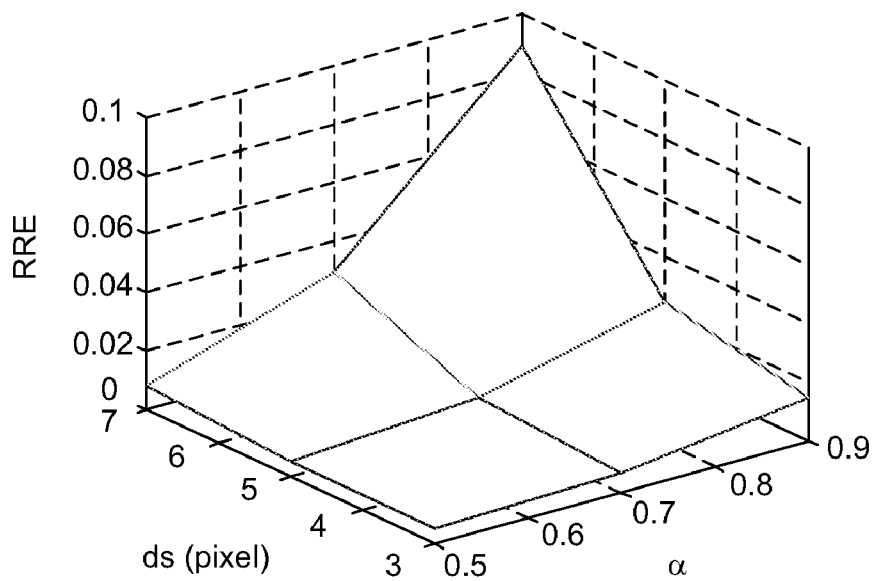
FIGS. 15A, 15B illustrate the RRE values of the reconstructions using different system parameters.
Figure 15B:
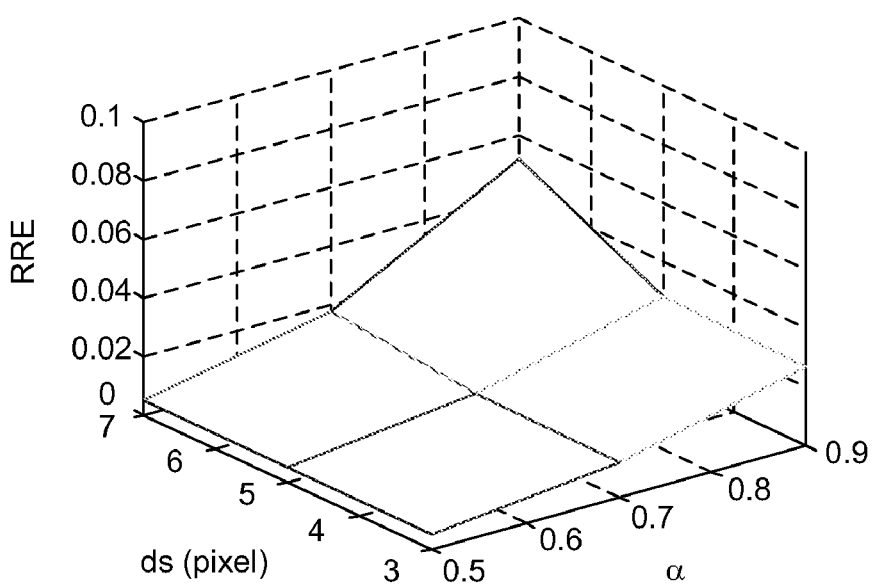

FIG. 15 also indicates that for an RRE below 3%, the blocker shadow size can be as large as ~5 mm. Considering the magnification factor of the modulator on the detector, the actual blocker size on the modulator is ~1 mm, if the system geometry of the physical experiments in Section IV-C is used. On the other hand, if a smaller d is achievable, α can be as high as 90%, in which case the exposure loss is only 5% (an issue for systems with limited x-ray tube output).

Note, however, that a simplified model is used in the simulations, and the performance of the algorithm will be limited in practice by the non-ideal effects of the system, such as penumbra effect due to the finite size of the focal spot, beam hardening effect etc. Therefore, the determination of d and α is based on considerations of the system physical limitations as well; the choice of $\omega_{max}$ does not change the physics of x-ray projection, and it could be optimized as a final step. The impact of the non-ideal effects on the algorithm performance with the suggested system parameters is currently under investigation.

Physical Experiments

The simulation experiments used a simplified model, mainly due to the computation complexity of MC simulation. Many issues that are important to practical implementations were not considered, such as the algorithm robustness to noise, effect of beam hardening on the algorithm etc. In particular, since a relatively low resolution (4 mm) phantom was used in the simulations, the resolution quality of the scatter corrected reconstructed image merits a closer examination. To provide additional validation of the proposed scatter correction algorithm, preliminary physical experiments were carried out on the table-top CBCT system in our lab.

Figure 16:
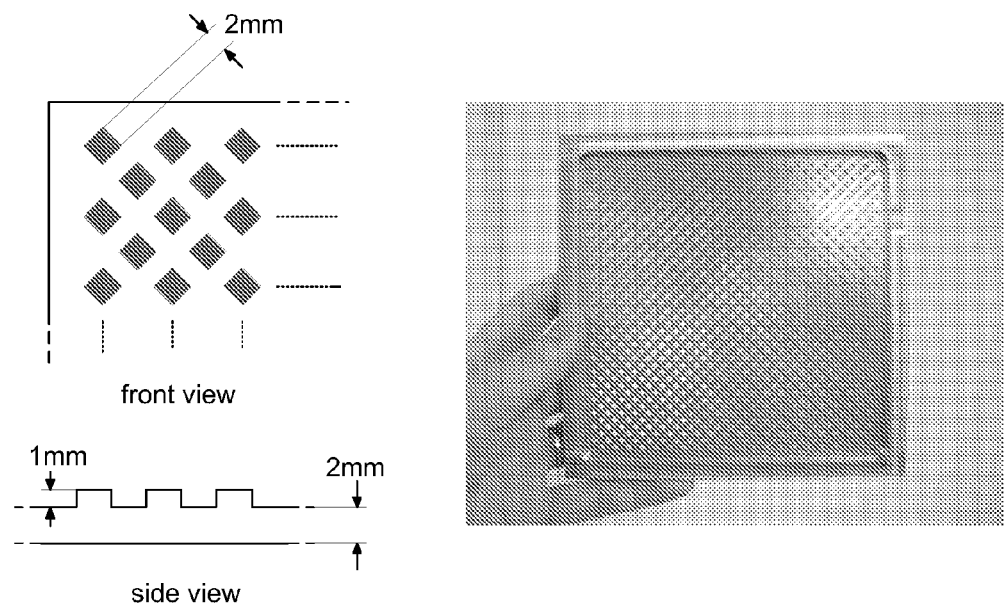
FIG. 16 illustrates the primary modulator used in the physical experiments.
Figure 17:
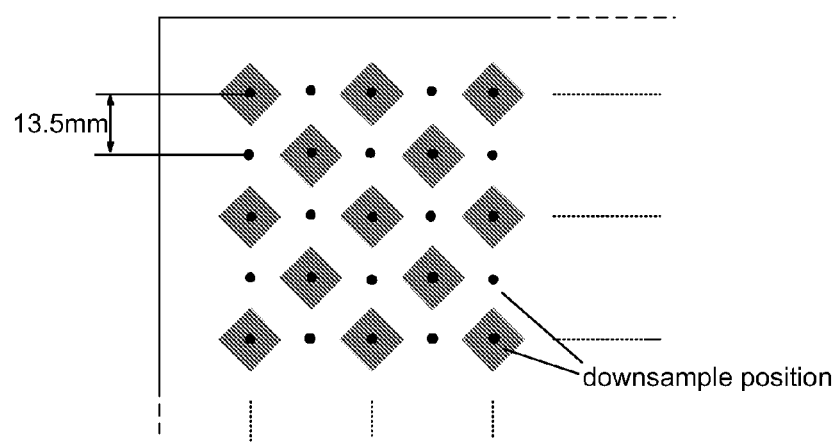
FIG. 17 illustrates the blocker shadow pattern on the detector and the downsample grid.

1) The Primary Modulator: Our first primary modulator was machined from aluminum. The geometry of the blockers is shown in FIG. 16. The blocker pattern is different from the checker-board pattern, due to manufacturing considerations. However, all the theories still apply, since we only process the downsampled data and the shape of blocker does not matter (see FIG. 17). The side length of the blocker square is 2 mm, its thickness is 1 mm, and the base of the modulator is 2 mm. Therefore the downsampling period on the detector in step 3.2 of the algorithm is $2\sqrt{2}$mm times the magnification factor from the primary modulator to the detector. The transmission of the blocker is approximately 90% when the x-ray source operates at 120 kVp. Note that, a larger blocker size is used, as compared to those used in the previous section. This is because the ratio of the blocker thickness to diameter must be small to avoid edge effects, while the blocker thickness cannot be smaller in order to keep the blocker transmission less than 90%. The low sampling rate of the blocker pattern limits the scatter correction capability when SPR and SPR variation are both very high. A more attenuating material could be used to provide a primary modulator with a higher sampling rate.

2) The Table-top System and Evaluation Phantom: The table-top CBCT system consists of a CPI Indico 100 100 kW programmable x-ray generator (CPI Communication & Medical Products Division, Georgetown, Ontario, Canada), a Varian G-1590SP x-ray tube (Varian X-ray Products, Salt Lake City, Utah), a rotation panel, a Varian PaxScan 4030CB flat panel a-Si large area x-ray detector, a workstation and shielding windows. The x-ray tube had a inherent filtration of 1.0 mm Al, and operated with a 0.6 mm nominal focal spot size. We mounted the primary modulator on the outside surface of the collimator, with a nominal distance to the x-ray focal spot of 231.0 mm. No anti-scatter grid was used in the experiments. The object was put on the panel, and it rotated during the scan to acquire data for different projection angles. The imaging and reconstruction parameters are summarized in Table II. Note that a relatively large mAs was used in the experiments to compensate for the extra filtration due to the 2 mm aluminum base of the modulator. Again, the FDK algorithm was used in the reconstructions, with the same Hamming-windowed ramp filter.

TABLE II

PARAMETERS OF THE PHYSICAL EXPERIMENTS

Imaging parameters:

| | |
|---|---|
| x-ray source | 0.6 mm nominal focal spot size |
| | 120 kV p, 35 mA |
| | pulse-fluro, 13 ms pulse width |
| source to detector distance | 1118.0 mm |
| source to rotation axis distance | 789.8 mm |
| source to modulator distance (nominal) | 231.0 mm |
| detector size | 400 mm-by-300 mm |
| | 1024-by-768 pixels |
| rotation | circular, 360 deg |
| number of views | 800 |

Reconstruction parameters:

| | |
|---|---|
| reconstructed voxel size | 0.391 mm in all directions |
| reconstructed volume size | 512-by-512-by-256 voxels |
| algorithm | FDK |

Figure 18:
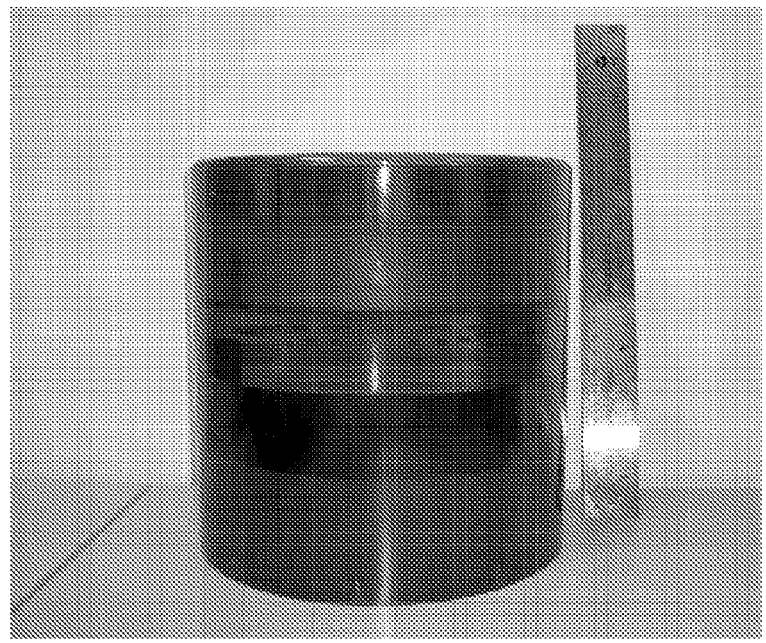
FIG. 18 illustrates the Catphan600 phantom.

A standard evaluation phantom, Catphan600 (The Phantom Laboratory, Salem, N.Y.), was used to investigate the performance of the scatter correction algorithm (see FIG. 18). A detailed description of the phantom can be found at: http://www.phantomlab.com/catphan.html. In order to show the possible impact on the image resolution of the algorithm, the plane of source trajectory was selected to coincide with the slice of the phantom that contains the resolution test gauge. The resolution test objects are located at a radius of 5 cm, and range in size from 1 to 21 line pairs per cm.

3) Preliminary Results: The pre-scans show that the blocker transmission has a mean value of 0.899 with a small variance. In the algorithm implementation, we assume that the transmission is the same for different blockers and the mean value is used as the parameter a. The pattern of the blocker shadows obtained in the pre-scan also indicate a sampling period of 13.5 mm. For the scatter correction results shown below, we use $$\omega max = \frac{\pi}{2}$$

as the cutoff frequency of the filter.

Figure 19:
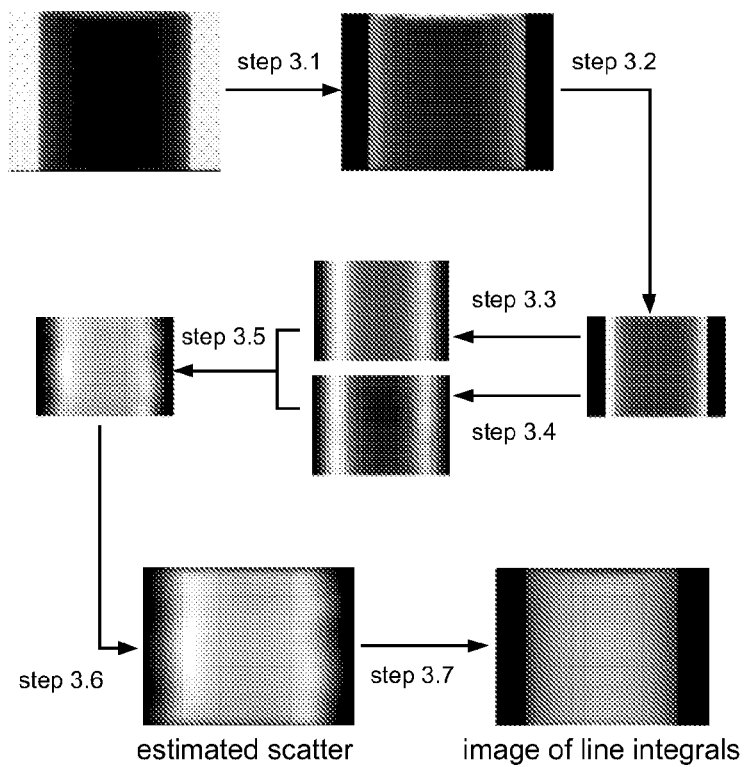
FIG. 19 is a diagrammatic illustration of the scatter correction on a projection image of the Catphan600 phantom.
Figure 20A:
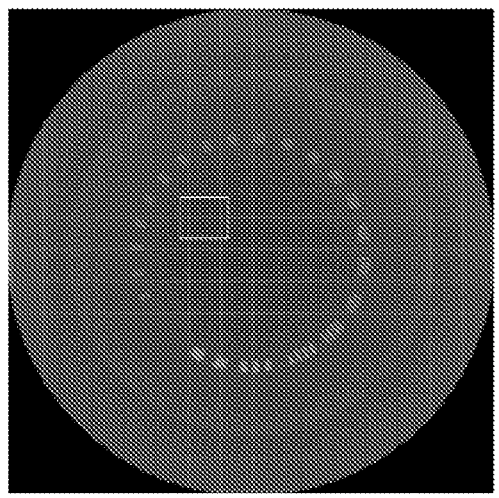
FIGS. 20A-20C illustrates experimental results of the Catphan600 phantom.
Figure 20B:
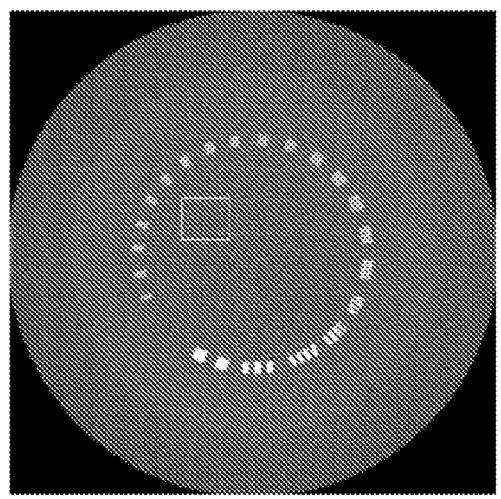
Figure 20C:
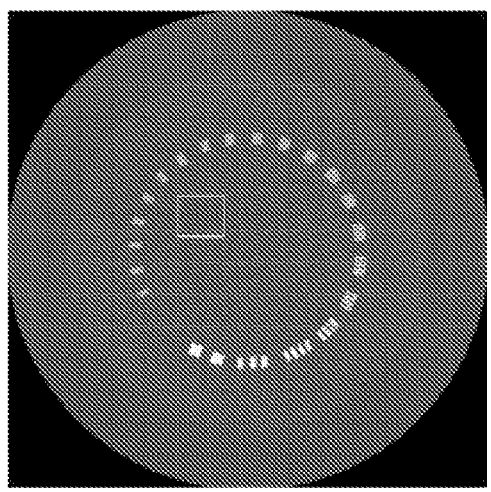
Figure 21:
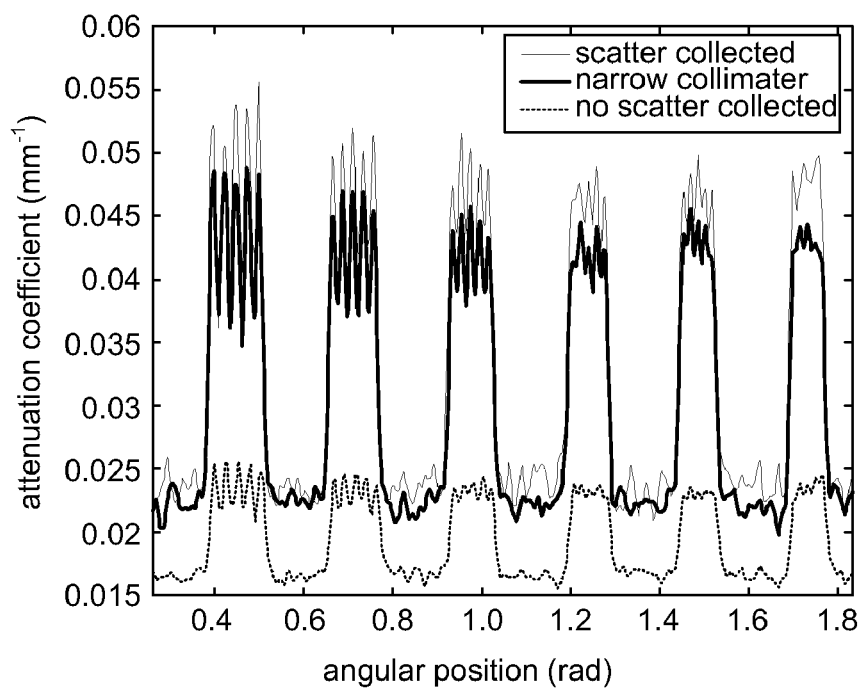
FIG. 21 illustrates the 1D profile comparison of FIG. 20.

A step-by-step illustration of the scatter correction algorithm on the projection images of the Catphan600 phantom is shown in FIG. 19, and the detailed description of each step is presented above. To provide a fair comparison, another experiment is also carried out with a 2 mm aluminum filter on the collimator, the same thickness as the base of the primary modulator, but without the modulator and the scatter correction. FIGS. 20(a) and 20(b) compare the two results, where the axial views are chosen to include the resolution test objects. As a reference, FIG. 20(c) is the same slice reconstructed from the projection data acquired with a narrowly opened x-ray source collimator with the aluminum filter as used in FIG. 20(a), and the beam width on the detector is about 10 mm. This imaging setup resembles a slot-scan geometry and the scatter is inherently suppressed. Note that a relative large display window is used to examine the visibility of the intense test objects. The comparison shows that the scatter is corrected effectively by the proposed algorithm using primary modulation. Referencing FIG. 20(c) as a "scatter-free" image, the primary modulation method reduces the reconstruction error in the central ROI (white squares) from 31.8% to 2.3%. Although the noise of the reconstructed image is changed (more discussion later), there is no noticeable impact on the resolution quality using the primary modulation. This conclusion is also supported in FIG. 21, which compares the 1D profiles of the images in FIG. 20, taken along the arc passing through the center of the test objects with the focus at the center of the images. The angular sampling rate is chosen such that the arc length between the samples is 0.0977 mm, one fourth of the reconstructed voxel size. The angle starts from $$\frac{\pi}{12} \text{ to } \frac{7\pi}{12}$$

(indicated by the white arcs in FIG. 20), one set of line pairs past the resolution supported by the angular sampling of the system, 1.2 lp/mm at a radius of 5 cm. The algorithm performance with respect to resolution is expected, since scatter is corrected by estimating low-frequency primary, and therefore only low frequency misestimation of primary is possible and the sharp transitions (high-frequency) between objects are preserved. A formal resolution study with a modulation transfer function (MTF) measurement is underway.

Figure 22:
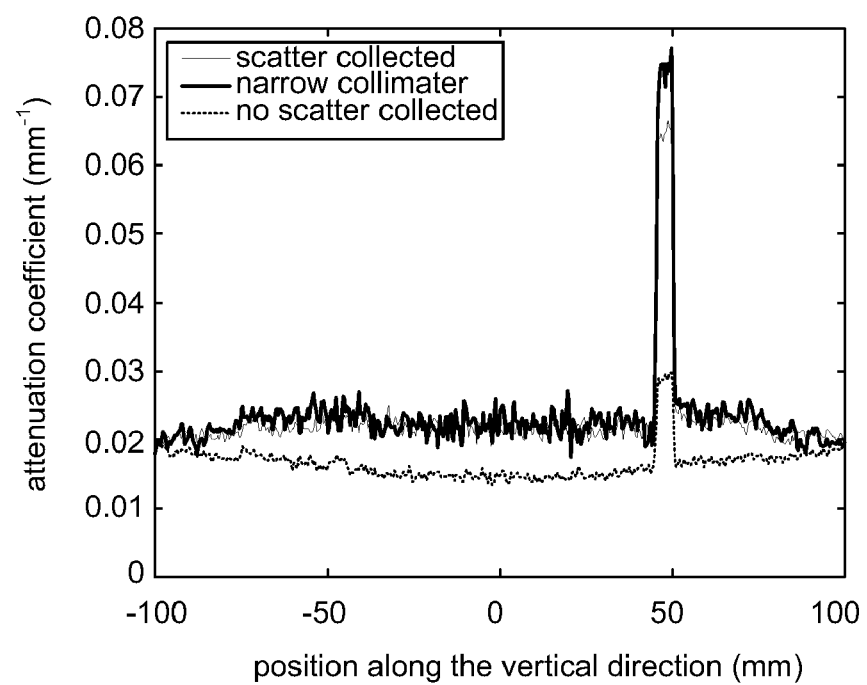
FIG. 22 illustrates the 1D profile comparison of FIG. 20, taken at the central vertical lines.

To provide further verification of effective scatter correction using our algorithm, FIG. 22 shows the 1D profiles taken at the central vertical lines of the images in FIG. 20. A good match is found between the result with scatter corrected using primary modulation and that with scatter greatly suppressed by a narrowly opened collimator. Both FIGS. 21 and 22 reveal that most of the difference is located in the dense objects and in their surrounding areas. This could be due to the residual scatter in the slot-scan geometry which results in more reconstruction error in the highly attenuating areas, the relatively large scatter estimation error around sharp transitions in the projection image, the beam-hardening effects that are not considered in the algorithm design etc.

4) Noise Analysis: Change of noise level is found in the selected ROI of reconstructed images in FIG. 20. This is because in the scatter estimation, low-frequency behavior of the scatter is assumed. Although the noise-free scatter distribution is usually smooth, the statistical noise of the scatter basically contains high-frequency signal and cannot be estimated using the proposed algorithm. The noise of scatter, therefore, is left in the primary estimate, increasing the noise in the reconstructed image. This problem is not specific to our proposed algorithm, and similar noise performance can be found in the reconstructed images of other scatter correction algorithms, as long as the same assumption of low-frequency scatter is made, and only a smooth (low-frequency) scatter estimate is removed from the recorded image.

The mathematics of the noise analysis of the projection data and reconstructed images can be found in classic textbooks. There are two types of noise to be considered in the projection image. One is the image independent noise due to the electrical and roundoff error; the other is the image dependent noise due to the statistical fluctuation of the x-ray photons that exit the object. We assume the noise of the first type is small, and only the second type is considered here.

Denote s and p as the random variables of the scatter and primary on the detector, respectively; and, s and p are poisson distributed with mean values S and P, i.e., s~poisson(S) and p~poisson(P). From the fact that the PSF of the scatter is broad and smooth, we assume s is independent of p, and therefore, (s+p)~poisson(S+P). Denote $I_0$ as the constant incident photon intensity. If no scatter correction is applied, the line integral image $q_l$ calculated by taking the negative log of the measured projection image can be written as:

$$q_l = \ln\left(\frac{I_0}{s+p}\right) \quad (6)$$
$$= -\ln(s+p) + \ln(I_0)$$

Denote $n_s$ and $n_p$ as the statistical noise of the scatter and primary, respectively, and express s and p as:

$$s = S + n_s$$
$$p = P + n_p \quad (7)$$

Plug into equation (6), and expand at (S+P):

$$q_l = -\ln(S+P) + \log(I_0) - \frac{1}{S+P}(n_s + n_p) + \quad (8)$$
$$O((n_s + n_p)^2)$$

Assume $(n_s+n_p)$ is small, and ignore the high order term, then the noise of $q_l$, $n_{nc}$, and its variance are approximated as:

$$n_{nc} \approx -\frac{1}{S+P}(n_s + n_p) \quad (9)$$

$$\text{var}(n_{nc}) \approx \frac{1}{S+P} \quad (10)$$

Similarly, if the proposed scatter correction algorithm is applied, the average profile S is corrected effectively, while $n_s$ is mostly intact. The noise in the line integral image, $n_c$, and its variance can be obtained as:

$$n_c \approx -\frac{1}{P}(n_s + n_p) \quad (11)$$

$$\text{var}(n_c) \approx \frac{1}{P}\left(1 + \frac{S}{P}\right) \quad (12)$$

Therefore, the ratio of the variance of $n_c$ and $n_{nc}$ is:

$$\frac{\text{var}(n_c)}{\text{var}(n_{nc})} \approx \left(1 + \frac{S}{P}\right)^2 \quad (13)$$

As a benchmark, an ideal scatter correction suppresses both S and $n_s$. Using the same method as above, we have similar expressions of the noise, $n_{ideal}$:

$$n_{ideal} \approx -\frac{1}{P}n_p \quad (14)$$

$$\text{var}(n_{ideal}) \approx \frac{1}{P} \text{ and,} \quad (15)$$

$$\frac{\text{var}(n_c)}{\text{var}(n_{ideal})} \approx \left(1 + \frac{S}{P}\right) \quad (16)$$

Equations (13) and (16) describe the quantitative relationship of the noise in the projection images of line integrals. The noise in the reconstructed image is the summation of the errors from different views, and the analysis is more involved. As a special case, in the physical experiments, we used a cylindrical phantom that is approximately circularly symmetric; therefore, the SPR distributions have small differences from view to view. Assuming the noise of the scatter and the primary are independent for different views, similar expressions of the noise variance of the reconstructed images around the center can be obtained as those of the projection images of line integrals, with an additional scaling determined by the filter, total projection number etc. Therefore, if the same filter kernel is used in the reconstruction, the equations (13) and (16) provide a rough approximation of the noise relationships in the central region of the reconstructed images. Since the slot-scan geometry inherently suppresses the scatter, it is close to the ideal scatter correction. Using equations (13) or (16), and the measured noise variances of the ROI's around the center of the reconstructed images, as shown in FIG. 20, we can calculate the corresponding SPR's as 2.41 or 1.95, respectively. On the other hand, based on the scatter estimation (step 3.6), the SPR around the central region of the projection image is estimated to be ~2.2, in good agreement with MC simulations of a water cylinder with the same diameter. Equations (13) and (16) are approximately consistent with the experimental measurements.

Discussion and Conclusions

We have presented a new practical and effective scatter correction method by primary modulation. A primary modulator with attenuating blockers arranged in a "checkerboard" pattern is designed and inserted between the x-ray source and the object. A scatter correction algorithm involving linear filtering techniques is developed for the modified x-ray system, with the hypothesis that the insertion of the primary modulator does not result in strong high-frequency components in the scatter distribution and only the primary distribution is modulated. Note that, although in this paper we implemented the proposed scatter correction technique for x-ray CT, it can also be used in other x-ray imaging applications, as long as a primary modulator can be inserted between the x-ray source and the imaged object. Recently, a similar frequency modulation based method was proposed by Bani-Hashemi et al. They inserted a modulation grid between the object and the detector and used non-linear filtering techniques to correct the scatter, based on the fact that the scatter and primary have very different responses to the modulation. In our method, it might be counter-intuitive that the modulator is placed where no scattering of the imaged object has occurred; however, a different rationale is used in the algorithm development. Our method is expected to be more dose efficient since in Bani-Hashemi's method, the modulation grid between the object and detector will absorb information carrying photons.

The key hypothesis of the algorithm was validated using a MC simulation, and the algorithm performance was evaluated by both MC simulations and physical experiments. The results show that the proposed method is able to suppress the scatter artifacts significantly. The MC simulations on the software humanoid phantom suggest system parameters for the physical implementation and reveals that the relative reconstruction error can be reduced from 74.2% to less than 1%. The scatter correction ability is also demonstrated by physical experiments, where a standard evaluation phantom was used. The proposed method reduces the reconstruction error from 31.8% to 2.3% in the central ROI. The image comparison also shows that the scatter correction method has no noticeable impact on the resolution of the reconstructed image. This is because in our method, only a low-frequency scatter estimate is subtracted from the original projection image, and the high frequency content is kept intact. This observation also makes our approach different from Bani-Hashemi's method. In their published studies, it has been reported that their technique will always produce a filtered image having at best 0.41 of the maximum detector resolution when maximum scatter rejection is desired. An analysis of the noise in the estimated projection images is also carried out. Since the high-frequency statistical noise in the scatter distribution can not be removed by our method, the noise of the line integral image using our method increases by a factor of (1+SPR), as compared to the noise of the image using perfect scatter correction. This noise increase is generally true for all of the scatter correction algorithms that assume smooth scatter distributions, such as most of the model-based correction methods, although it can be avoided in the scatter suppression methods that use the property of the scatter incident angle, such as anti-scatter grid, air-gap etc.

Our implementation uses a calibration sheet with a "checker-board" pattern, and only the data at the center of blocker shadows are used in the scatter correction to avoid edge effects. Note, however, that other patterns can also be designed based on different modulation functions. For example, a high-frequency sinusoidal function is free of edges, and it can be used to avoid the downsample/upsample steps in the algorithm.

Our approach has several advantages. First, requiring only an insertion of a stationary calibration sheet, this approach is easy to implement. Second, the semi-transparency of the blockers reduces the loss of exposure, and it enables sampling of the field distribution with a higher sampling rate, as compared to the measurement based correction using a beam stop array. As a result, the scatter estimation is expected to be more accurate. Third, a single scan is necessary to acquire both the primary and the estimate of the scatter, and the primary modulator is placed between the x-ray source and the object, so the dose required for an acquisition is the same as for a conventional scan with no anti-scatter grid. Fourth, since the primary is modulated, not completely blocked, realtime imaging algorithms could be implemented so that the visual effects of the checkerboard pattern are not seen during image acquisition. Fifth, this approach uses linear filtering techniques, therefore the computation can be very efficient.

Attached as an appendix is a paper by Zhu, Bennett and Fahrig titled "Scatter Correction Method for X-Ray CT Using Primary Modulation: Theory and Preliminary Results" which is incorporated herein by reference for all purposes.

What is claimed is:

1. In x-ray imaging, a method of spatial frequency translating a detected signal from a primary x-ray source for separation from low frequency scatter radiation signal comprising the steps of:
   a) amplitude modulating the x-ray beam from a primary x-ray source thereby creating a side band of a high-frequency primary signal with frequency equal to the sum of frequency of the modulation and frequency of the x-ray beam,
   b) detecting the side band, whereby the side band frequency is spaced from low frequency scatter radiation;
   c) estimating a low-frequency primary signal from the detected side band of the high-frequency primary signal; and
   d) using the estimated low-frequency primary signal to estimate scatter.

2. The method of claim 1 wherein step a) employs a sheet having a repetitive pattern of material with different x-ray attenuation through which the x-ray beam is directed, wherein the sheet is placed between an x-ray source and an object to be imaged.

3. The method of claim 2 wherein the repetitive pattern comprises a checkerboard pattern of material having different x-ray attenuation whereby the x-ray beam is modulated in amplitude in accordance with the spacing of the checkerboard pattern.

4. In the processing of detected x-rays from a primary X-ray source and separating the detected scatter radiation signal from a detected signal, a method comprising the steps of:
   a) amplitude modulating x-rays from a primary x-ray source,
   b) detecting amplitude modulated radiation,
   c) low pass filtering the detected signals from step b) to obtain a scatter signal and a low frequency portion of a spectrum of a detected primary signal,
   d) high pass filtering the detected signals from step b) to obtain a measure of a high frequency portion of the detected signals,
   e) demodulating the high pass filtered detected signals from step d) to obtain a measure of low frequency portion of the spatial spectrum of the detected primary signal, and
   f) subtracting a weighted measure of the low frequency portion from step e) from the low pass filtered detected signals from step c) to provide a measure of scatter radiation signal.

5. The method of claim 4 wherein step a) includes passing x-rays from the primary source through a sheet having a repetitive pattern of material with different x-ray attenuation through which the x-ray beam is directed, and then through an imaged object.

6. The method of claim 5 wherein the repetitive pattern comprises a checkerboard pattern of material, having different x-ray attenuation whereby the x-ray beam is modulated in amplitude in accordance with the spacing of the checkerboard pattern.

7. The method of claim 4 and further including the step of:
   g) Fourier transforming the measure of scatter radiation to k-space.

8. The method, as recited in claim 4 further comprising before step c performing a boundary detection algorithm to suppress a high frequency primary signal.

9. The method, as recited in claim 8, further comprising performing a soft cutoff process.

10. Apparatus for use in separating scatter radiation in an x-ray imaging system in which radiation from an x-ray source passes through an imaged object to an x-ray detector comprising:
    a) a sheet having a repetitive pattern of material with different radiation attenuation through which the radiation passes thereby amplitude modulating the radiation at a modulation frequency determined by the pattern repetition, wherein the sheet is placed between the x-ray source and the imaged object,
b) a high pass filter for separating high frequency signals from the detector,
c) a demodulator for shifting high frequency signals to lower frequencies, thereby providing a measure of low frequency primary signal without low frequency scatter signal.

11. Apparatus of claim 10 and further including:
d) a subtractor for subtracting the measure of low frequency primary signal from a combined measure of detected scatter signal and low frequency primary signal from detected from the x-ray beam, thereby providing a measure of scatter radiation signal.

12. Apparatus of claim 11 and further including:
e) means for weighting the measure of low frequency primary signal by a factor depending on the attenuation of the repetitive pattern prior to subtracting from the combined measure of detected scatter signal and low frequency primary signal.

* * * * *

UNITED STATES PATENT AND TRADEMARK OFFICE
CERTIFICATE OF CORRECTION

| | | |
|---|---|---|
| PATENT NO. | : 7,463,712 B2 | Page 1 of 1 |
| APPLICATION NO. | : 11/557440 | |
| DATED | : December 9, 2008 | |
| INVENTOR(S) | : Zhu et al. | |

It is certified that error appears in the above-identified patent and that said Letters Patent is hereby corrected as shown below:

In the Specification Under Column 1:

Please replace Column 1, Line No. 16-18 with

--This invention was made with Government support under contract EB003524 awarded by the National Institutes of Health. The Government has certain rights in the invention.--

Signed and Sealed this
Twenty-sixth Day of April, 2016

Michelle K. Lee
*Director of the United States Patent and Trademark Office*